US011149079B2

(12) United States Patent
More et al.

(10) Patent No.: US 11,149,079 B2
(45) Date of Patent: Oct. 19, 2021

(54) PROCESS FOR THE PREPARATION OF IMMUNOGLOBULIN G (IGG)

(71) Applicant: BIO PRODUCTS LABORATORY LIMITED, Elstree (GB)

(72) Inventors: John More, Elstree (GB); Tara Dolan, Elstree (GB)

(73) Assignee: BIO PRODUCTS LABORATORY LIMITED, Elstree (GB)

( * ) Notice: Subject to any disclaimer, the term of this patent is extended or adjusted under 35 U.S.C. 154(b) by 72 days.

(21) Appl. No.: 15/328,996

(22) PCT Filed: Jul. 24, 2015

(86) PCT No.: PCT/GB2015/052144
§ 371 (c)(1),
(2) Date: Jan. 25, 2017

(87) PCT Pub. No.: WO2016/012803
PCT Pub. Date: Jan. 28, 2016

(65) Prior Publication Data
US 2017/0247433 A1 Aug. 31, 2017

(30) Foreign Application Priority Data
Jul. 25, 2014 (GB) .................................... 1413227

(51) Int. Cl.
*C07K 16/06* (2006.01)
(52) U.S. Cl.
CPC ................... *C07K 16/065* (2013.01)
(58) Field of Classification Search
None
See application file for complete search history.

(56) References Cited

U.S. PATENT DOCUMENTS

| 2,437,060 | A | 3/1948 | Williams et al. |
| 4,246,085 | A | 1/1981 | Mattock |
| 8,466,265 | B2 | 6/2013 | Cox |
| 8,993,734 | B2 * | 3/2015 | Bruckschwaiger .. A61K 9/0019 530/412 |
| 9,718,856 | B2 | 8/2017 | Chtourou et al. |
| 9,782,477 | B2 * | 10/2017 | Bruckschwaiger .. A61K 39/395 |

FOREIGN PATENT DOCUMENTS

| AU | 715427 B2 | 9/1997 |
| CN | 101648998 A | 2/2010 |
| EP | 0078331 A1 | 5/1983 |
| EP | 0764658 A1 | 3/1997 |
| JP | 601134 A | 1/1985 |
| UA | 45557 U | 11/2009 |
| WO | 97/32654 | * 9/1997 |
| WO | 9732654 | 9/1997 |
| WO | 2008068455 A1 | 6/2008 |
| WO | 2008113589 A1 | 9/2008 |
| WO | 2010132686 A1 | 11/2010 |
| WO | 2012080422 A1 | 6/2012 |
| WO | 2013126904 A1 | 8/2013 |
| WO | 2013132053 A1 | 9/2013 |

OTHER PUBLICATIONS

Andrea Buchacher and Waltrud Kaar,Production of Plasma Proteins for Therapeutic Use, Ch. 13, John Wiley & Sons, Inc., 2013, Editors Joseph Bertolini, Neil Goss and John Curling.
Cohn, E.J. et al., Preparation and Properties of Serum and Plasma Proteins. IV. A System for the Separation into Fractions of the Protein and Lipoprotein Components of Biological Tissues and Fluids1a,b,c,d. J. Am. Chem. Soc., 68:159-475, (1946).
J. A. Hooper, Intravenous immunoglobulins: evolution of commercial IVIG preparations. Immunol. Allergy Clin. N. Am. 28 (2008) 765-778.
Korneyeva et al., Enveloped Virus Inactivation by Caprylate: A Robust Alternative to Solvent-Detergent Treatment in Plasma Derived Intermediates. Biologicals, Academic Press Ltd., vol. 30, No. 2, Jun. 1, 2002, pp. 153-162.
Martin et al., IGIV: Contents, properties, and methods of industrial production—evolving closer to a more physiologic product. International Immunopharmacology, vol. 6, No. 4, 2006, pp. 517-522.
Oncley, J.L. et al., The Separation of the Antibodies, Isoagglutinins, Prothrombin, Plasminogen and β1-Lipoprotein into Subfractions of Human Plasma. J. Am. Chem. Soc., 71, 541-550, (1949).
P. Kistler and Hs. Nitschmann, Large Scale Production of Human Plasma Fractions : Eight Years Experience with the Alcohol Fractionation Procedure of Nitschmann, Kistler and Lergier. Vox Sang. 7: 414-424 (1962).
Roberts et. al., Development of an intravenous immunoglobulin with improved safety and functional activity Original Research Article, vol. 43(2), Mar. 2015, p. 123-129.
Tanaka et al., High Quality Human Immunoglobulin G Purified From Cohn Fractions by Liquid Chromatography. Brazilian Journal of Medical and Biological Research, vol. 33, No. 1, Jan. 1, 2000, pp. 27-30.
Liu et al., Purification of human immunoglobulins A, G and M from Cohn fraction II/III by small peptide affinity chromatography Journal of Chromatography A, vol. 1262, Nov. 1, 2012, pp. 169-179.
Rousell and McCue—Antibody Purification From Plasma, Blood Separation and Plasma Fractionation, p. 307-340, 1991, Wiley-Liss, Inc., Ochs HD, Siegel J. Stabilizers used in intravenous immunoglobulin products: a comparative review, Pharmacy Practice News. Special Reports, 2010.

(Continued)

*Primary Examiner* — Patricia Duffy
(74) *Attorney, Agent, or Firm* — Stinson LLP

(57) ABSTRACT

The present invention is directed to processes for extracting IgG from an unused waste precipitate produced during normal plasma fractionation processes via a separate fractionation process, thereby increasing the overall yield of IgG from blood plasma.

21 Claims, 5 Drawing Sheets

(56) References Cited

OTHER PUBLICATIONS

Ochs et al., Stabilizers Used in Intravenous Immunoglobulin Products: A Comparative Review, Pharmacy Practice News, Special Report, pp. 1-8.
Curling, J.M., Methods of Plasma Protein Fractionation; Pharmacia Fine Chemicals, 1980. 16-pages.
European Pharmacopoeia, Fifth Edition, vol. 2; 7-pages.
Declaration of Dr. Wolfgang Teschner, Opposition Proceedings of EP3071596, filed Oct. 8, 2020.
Matteson and Orr, Filtration—Principles and Practices, 2nd edition, edited by Marcel Dekker, Inc., New York, Basel, 1987, top pages and p. 309.

\* cited by examiner

PROCESS FOR THE PREPARATION OF IMMUNOGLOBULIN G (IGG)

This application claims priority to International Application Number PCT/GB2015/052144, filed on 24 Jul. 2015, which claims benefit of GB Patent Application Serial No. 1413227.8, filed 25 Jul. 2014, the disclosures of which are hereby expressly incorporated by reference in their entireties.

The present invention relates to improved processes for the preparation of immunoglobulin G (IgG).

BACKGROUND

Immunoglobulin G (IgG) is an abundant antibody isotype in humans. IgG binds to many different kinds of pathogens, including viruses, bacteria and fungi, to protect the body from infection. Thus, IgG plays a key role in the function of the immune system. There are four IgG subclasses in humans: IgG1, IgG2, IgG3 and IgG4. IgG1 and IgG2 are the most common types of IgG, accounting for nearly 90% of all IgG. For ease of reference, in this document, where IgG is referred to, it is intended to encompass all four types, as well as any combinations thereof. The term "IgG" is further intended to encompass IVIG (intravenous immunoglobulin), SCIG, (subcutaneous immunoglobulin) and IMIG (intramuscular immunoglobulin).

As noted above, IgG plays a key role in the function of the immune system. It has been found that patients with immune and autoimmune disorders can benefit from treatment with IgG. Conditions that may be treated with IgG include primary immunodeficiency (PID), including severe combined immunodeficiency (SCID) and common variable immunodeficiency (CVID), and secondary immunodeficiencies (SID) resulting from other illnesses such as chronic lymphocytic leukaemia, multiple myeloma or paediatric AIDS or following bone marrow transplantation. Other conditions which may be treated include idiopathic thrombocytopenic purpura (ITP), Kawasaki's disease, systemic lupus erythematosus (SLE), Myasthenia Gravis, chronic inflammatory demyelinating polyneuropathy (CIDP), and multifocal motor neuropathy (MMN). IgG is also used in the treatment of numerous other rheumatological, haematological and dermatological conditions.

IgG is normally isolated from pooled human blood plasma using conventional fractionation processes. A cold ethanol fractionation process was developed by Cohn in the early 1940 s to purify albumin from human blood (Cohn, E. J. et al., J. Am. Chem. Soc., 68: 459-475, (1946)). This is also known as 'Cohn Method 6'.

This process is based on the differential solubility of the desired proteins based on pH, ethanol concentration, temperature, ionic strength and protein concentration. During the Cohn process, the ethanol concentration increases up to 40%, the pH decreases from neutral to 4.8 and the temperature decreases from room temperature to −5° C. over the course of the fractionation. As conditions change during the process, different plasma proteins precipitate out sequentially, with other proteins remaining in solution. Depending on the exact protein(s) of interest, either or both of the precipitate and the supernatant from each fractionation step may be further processed. There are five major Cohn precipitate fractions, fractions I to V, with each fraction comprising a different protein as its major component. For example, albumin is obtained from fraction V, while IgG can be obtained from fraction II+III. Subsequently a method for further sub-fractionation of Cohn Fraction II+III (an intermediate of Cohn Method 6) into Fraction II (a more purified IgG precipitate fraction) was developed and is referred to as 'Oncley Method 9' (Oncley, J. L. et al., J. Am. Chem. Soc., 71, 541-550, (1949)).

There are many variations on the Cohn process, including the Gerlough, Hink and Mulford methods. The Kistler & Nitschmann method is another well-known variant (P. Kistler and Hs. Nitschmann, Vox Sang. 7: 414-424 (1962)). In this method, precipitates A to C replace Cohn fractions II+III, III and V respectively. This process has been widely accepted because it involves fewer steps overall than in the Cohn method, with benefits of faster processing and lower ethanol usage.

Other methods to purify IgG include direct isolation of IgG from plasma or plasma intermediate II+III from Cohn Method 6 by ion-exchange chromatography and polyethylene glycol precipitation. Yields from the processes can be relatively high.

Some of these methods have been discontinued amid concerns about purity and in particular the transmission of blood-borne viruses such as hepatitis and HIV. However, the introduction of specific virus inactivation steps has led to substantial investment in chromatographic processes in recent years, although the complexity, high capital costs and high water/waste treatment requirements has limited this option to all but the largest and most well financed plasma fractionators.

The Cohn process (and variants thereof) produce substantially monomeric IgG. By this it is meant that the majority of the IgG product is monomeric, with less than 20% of the IgG in the form of dimers and larger aggregates. In general, the presence of IgG aggregates is undesirable, as it has been linked to unwanted immune responses in patients receiving IgG derived from plasma. It is therefore desirable for the IgG product obtained by any purification process to contain as much monomer as possible.

Demand for IgG more than doubled between 1998 and 2006, and demand continues to grow. In 2008, the global market for plasma fractions was estimated at US$12 billion, with almost half of that being IgG. At present, supply must come from plasma donated by human donors. As there is a finite supply of plasma, there is consequently a need in the art for improved processes for isolating IgG having improved yield. However, for all clinical applications, it is important to have highly pure IgG in order to minimise any undesirable side effects resulting from, for example, the presence of other proteases or clotting factors, or other contaminating components, such as blood-borne viruses.

J. A. Hooper, in Immunol. Allergy Clin. N. Am. 28 (2008) 765-778, and Andrea Buchacher and Waltrud Kaar in Chapter 13 of Production of Plasma Proteins for Therapeutic Use (John Wiley & Sons, Inc., 2013, Editors Joseph Bertolini, Neil Goss and John Curling) describe various processes for preparing commercial IgG formulations. The majority of the IgG products licensed for use are produced by cold ethanol fractionation (i.e. the Cohn/Oncley process or a variant thereof) followed by purification using ion exchange chromatography. IgG losses are minimised by use of I+II+III (or II+III if fibrinogen is precipitated earlier in fraction I) as the starting material for ion exchange chromatography as the main loss of IgG occurs at the subsequent Fraction III (Precipitate B) stage of the Cohn/Oncley (Kistler & Nitschmann) fractionation process.

It is inherent in any protein purification scheme that the target protein is separated from any unwanted proteins and any other unwanted matter that is then deemed superfluous to the process. Such other matter may comprise other chemical moieties including hazardous or pathogenic substances which are undesirable in the target product. Thus, protein purification processes generally produce a "product fraction" containing the protein(s) of interest and so-called "waste" or "side" fractions. However, such dismissive classifications can be misleading because these so-called "waste fractions" may nevertheless have value as source materials for other proteins or component substances.

In the field of plasma proteins, evidence for this misleading nomenclature is found in AU715427B2, that describes use of "waste fractions" as a feedstock for purification of specific immunoglobulins by affinity chromatography. Similarly, JPS601134A describes the use of waste fractions as a feedstock for purification of immunoglobulins by gradient electrophoresis. WO2010/132686A1 describes the use of a discarded fraction from IgG fractionation to purify aggregated immunoglobulins which are present in that fraction.

UA45557U demonstrates an alternative use of the term "waste fraction" by describing a normal plasma fractionation processes that is applied to plasma donations which have been rejected as "waste" due to contamination with markers of the hepatitis C pathogen.

There remains an unresolved problem that IgG yields in the Cohn/Oncley process and variants thereof (hereafter referred to as the main process stream) are less than the total amount of IgG present in plasma. This may reflect some denaturation of the protein during the manufacturing process. Additionally or alternatively, small residual amounts of high-quality immunoglobulin (i.e. non-aggregated, predominantly monomeric IgG) may be separated from the main manufacturing fractionation pathway by entrapment in separated and removed "waste" fractions which also contain other components including multimeric and aggregated IgG.

This compromises efficient recovery of valuable immunoglobulin from the scarce plasma starting material, with consequent impact on availability of therapeutic product for the benefit of patients.

In the context of this application, the term "waste fraction" is defined as a fraction which is separated from the desired "main product fraction". The product fraction will typically contain the desired target protein in high purity. The so-called waste fraction will contain some of the target protein, albeit in combination with other components which may compromise the quality, efficacy or safety of the target protein. The waste fraction may in fact be of value as a source of proteins other than the target protein. In this application, the target protein is the immunoglobulin IgG.

Thus, in the purification of plasma to extract IgG, the main process stream is that leading to the IgG product. If the main process is a Cohn fractionation process, then the main product fraction is Cohn fraction II. In a Cohn fractionation process to produce IgG, supernatant A+I would be considered to be "waste" as it does not contain a significant amount of IgG. However, as demonstrated in FIG. 1, such a waste product can be further purified to yield other target proteins. For example, supernatant A+I can be further processed to yield Cohn fraction V, containing albumin. Thus, supernatant A+I is only a "waste fraction" when the primary protein of interest from the plasma fractionation process is anything other than albumin.

It has been found that waste fractions generated during the Cohn/Oncley process (and variants thereof) can contain significant amounts of IgG. It has been shown that the waste fractions may contain as much as 30% of the total amount of IgG in the starting plasma.

It would be advantageous to provide improved processes for producing IgG that can have higher yields than currently available processes while maintaining high levels of purity and safety, and which do not require additional complex and expensive chromatography steps.

SUMMARY OF THE INVENTION

It has now surprisingly been found that IgG of high purity (e.g. complying with the European Pharmacopoeia monograph 0338 for normal immunoglobulin comprising not less than 85 wt. % monomer and dimer and not more than 10 wt. % polymer and/or aggregate) can be relatively easily obtained from precipitate fractions which were previously considered as "waste" fractions during plasma fractionation processes to produce IgG, without the need for chromatography steps, and particularly without the need for affinity or anion exchange chromatography steps. By extracting IgG from such waste fractions, the overall yield of IgG can be significantly increased, without the need for additional subsequent purification steps.

The present invention therefore provides use of a waste precipitate fraction produced during plasma fractionation as a source of IgG. Preferably, the waste precipitate fraction is produced during a fractionation step to produce a liquid fraction (supernatant) containing IgG.

More specifically, the invention provides a method for extracting IgG from a waste precipitate fraction produced during plasma fractionation and separated from the main IgG manufacturing process stream, the method comprising contacting the waste precipitate with a suitable solvent to extract IgG from the waste precipitate. Preferably, the waste precipitate fraction is produced during a fractionation step to produce a liquid fraction (supernatant) containing IgG. In particular, the method of the invention does not require any chromatography steps, such as affinity chromatography or anion exchange chromatography, and no electrical processes, such as electrophoresis, for separation of the IgG from a waste precipitate fraction produced during plasma fractionation.

In another aspect, the invention provides a method for improving the yield of IgG during plasma fractionation to produce IgG, the method comprising extracting IgG from a waste precipitate fraction which is produced during plasma fractionation and separated from the main IgG manufacturing processing stream, using a suitable solvent. Preferably, the waste precipitate fraction is produced during a fractionation step to produce a liquid fraction (supernatant) containing IgG.

In another aspect, the invention provides a method for the separation of IgG from plasma or a plasma fraction, the process comprising
  a) fractionating the plasma or plasma fraction to produce a liquid fraction containing a majority of the IgG in the plasma or a plasma fraction, and a waste precipitate fraction containing additional IgG; and
  b) extracting at least some of the additional IgG from the waste precipitate fraction using a suitable solvent.

In a preferred aspect, the invention provides a method for the preparation of IgG comprising:
  a) recovering precipitate and supernatant from a modified Kistler and Nitschmann B+I fractionation process;
  b) homogenising the precipitate obtained in step a) and extracting IgG therefrom by mixing with 17 vol. % ethanol in aqueous acetate/phosphate buffer at 0° C. for 1 to 3 hours; and then
  c) separating the buffer containing extracted IgG from any remaining precipitate.

More preferably, the method above further comprises combining the buffer containing extracted IgG obtained in step c) with the modified Kistler and Nitschmann B+I supernatant obtained in step a). Alternatively, in the method described above, step c) is performed via filtration and the method further comprises incubating the extracted IgG in aqueous ethanol according to the conditions for Kistler and Nitschmann Fraction II precipitation; and recovering the resulting IgG-enriched Fraction II precipitate.

In all aspects of the invention, the waste precipitate fraction is preferably substantially equivalent to Cohn fraction III. More preferably, it is Cohn fraction III or I+III, Kistler & Nitschmann precipitate B or B+I, or modified Kistler & Nitschmann precipitate B or B+I.

In all aspects of the invention, the liquid fraction is preferably substantially equivalent to Cohn supernatant III. More preferably, it is Cohn supernatant III or I+III, or Kistler & Nitschmann supernatant B or B+I, or modified Kistler & Nitschmann supernatant B or B+I. Most preferably, the liquid fraction can be reintroduced into the mainstream Cohn supernatant III or I+III or modified Kistler & Nitschmann supernatant B or B+I for onward downstream processing of the IgG. It may also be processed onward as a separate sub-fraction and reintroduced into the mainstream processing at Fraction II or after further downstream processing at any suitable subsequent stage. Alternatively, the liquid fraction could be processed entirely independently through to a purified human IgG product.

Any reference herein to a modified Kistler & Nitschmann process is referring to a process such as that described in Roberts et. al., Biologicals, Vol. 43(2), March 2015, p 123-129.

DETAILED DESCRIPTION

Figure 1:
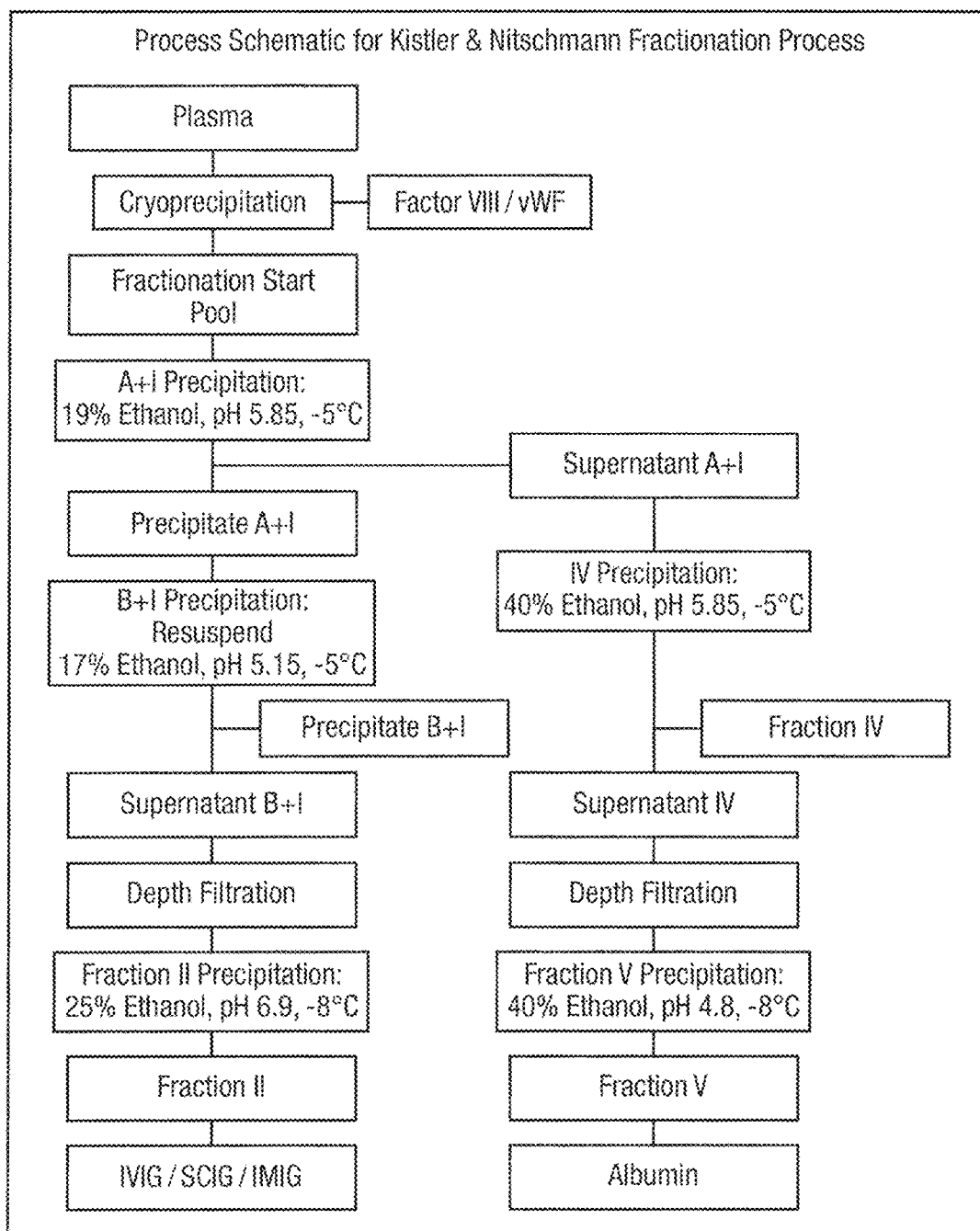
FIG. 1 is a schematic of a modified Kistler & Nitschmann cold ethanol fractionation process which can be used for the production of human IgG and albumin.

In the following, the terms "liquid fraction" and "supernatant" are equivalent, as are the terms "precipitate" and "fraction".

The IgG products obtained in the methods described herein are of high purity, with minimal aggregated IgG, and therefore meet the minimum standards for purity set out the European Pharmacopoeia monograph 0338 (January 2015). Thus, the IgG products directly obtained by the methods described herein contain at least 90% gammaglobulin, as determined by electrophoresis. The product obtained by these methods also contains at least 85 wt. % monomeric and dimeric IgG, with less than 10 wt. % of polymeric and aggregated IgG, as determined by size exclusion chromatography. HPLC may also be used to analyse aggregate content. This means that the products obtained from the fractionation processes described herein are of sufficient purity and quality to meet European pharmacopoeial standards, and therefore do not necessarily require any further purification to form a pharmaceutical product. Of course, the IgG obtained by the fractionation processes described herein may be further processed by any suitable means to obtain a higher quality IgG product, or to obtain a different product profile e.g. for an alternative pharmaceutical use. Such further processing methods are well known to the person skilled in the art, and may include in particular one or more virus inactivation steps.

Cold ethanol fractionation is one of the most widely used methods for isolating IgG from blood plasma. Generally, a pooled batch of plasma from multiple donors is subjected to cryoprecipitation to remove clotting factors such as Factor VIII as cryoprecipitate. The cryoprecipitate supernatant is then subjected to one or more cold ethanol fractionation steps to eventually produce a precipitate fraction comprising primarily IgG. In both the classic Cohn/Oncley process and the Kistler & Nitschmann method, this IgG-rich fraction is referred to as Fraction II or precipitate II. This precipitate is then subjected to further purification and virus inactivation steps to provide a pharmaceutically acceptable IgG final product, for intravenous, subcutaneous or intramuscular infusion.

"Normal plasma", "hyperimmune plasma" (such as hyperimmune anti-D, tetanus or hepatitis B plasma) or any plasma equivalent thereto can be used in the cold ethanol fractionation processes described herein.

In the Cohn fractionation method, the first fractionation step results in fraction I which comprises mainly fibrinogen and fibronectin. The supernatant from this step is further processed to precipitate out fraction II+III and then fractions III and II. Typically, fraction II+III contains approximately 60% IgG, together with impurities such as fibrinogen, IgM, and IgA. Most of these impurities are then removed in fraction III, which is considered a waste fraction and is normally discarded. The supernatant is then treated to precipitate out the main IgG-containing fraction, fraction II, which can contain greater than 90% IgG. The above % values refer to % purity of the IgG. Purity can be measured by any method known in the art, such as gel electrophoresis.

In the Kistler & Nitschmann method, fraction I is equivalent to fraction I of the Cohn method. The next precipitate/fraction is referred to as precipitate A (fraction A). This precipitate is broadly equivalent, although not identical, to Cohn fraction II+III. The precipitate is then redissolved and conditions adjusted to precipitate out precipitate B (fraction B), which is equivalent to Cohn fraction III. Again, this is considered to be a waste fraction, and is normally discarded. The precipitate B supernatant is then processed further to produce precipitate II, which corresponds to Cohn Fraction II.

In a modification of the Kistler & Nitschmann process, shown in FIG. 1, it is possible to combine the first two fractionation steps such that fraction I is not recovered and the first precipitate, which is referred to as A+I, includes fibrinogen and fibronectin. When this precipitate is resuspended and subjected to a further precipitation step, the precipitate formed, which can be referred to as B+I, contains fibrinogen and fibronectin as well as other impurities including IgM and IgA. The supernatant from this precipitation step is then further processed to produce the IgG-rich fraction, Fraction II. The B+I precipitate in this process is also considered to be a waste fraction insofar as the IgG process stream is concerned.

In principle, the methods of the present invention may be applied to any of the precipitate fractions produced during cold ethanol fractionation prior to production of fraction II, including Cohn fraction III and fraction I+III and Kistler & Nitschmann precipitate B or B+I. Preferably, the methods are applied to the precipitate fraction immediately preceding fraction II in the fractionation process, which is normally considered a waste fraction. Preferably, the waste precipitate fraction is Cohn fraction III or I+III, Kistler & Nitschmann precipitate B or B+I, a modified Kistler & Nitschmann precipitate B or B+I, or a fraction which is substantially equivalent thereto.

It has been found that these waste precipitate fractions can contain significant amounts of the IgG from the starting plasma pool, in some cases as much as 25-30%. This is postulated to be due in part to some supernatant being trapped in the precipitate fraction and in part due to co-precipitation of IgG with impurities such as IgM and IgA.

Surprisingly, it has been found that it is possible to recover a commercially significant proportion of the "lost" IgG in relatively pure form through a simple washing (extraction) process applied to the waste fraction. This result is unexpected, as a skilled person would have expected that extracting IgG from waste precipitate would be difficult given the relatively high levels of other proteins present in the precipitate, and that any IgG that could be extracted would be of low purity (e.g. in terms of aggregation and other unwanted protein species or proteolytic activity).

It is important to note that the method of the present invention does not require any chromatographic steps to extract further IgG from the waste fraction. Thus, the process of the present invention provides a relatively pure IgG product from waste fractions without the need for chromatography.

Choice of a suitable solvent for the washing process has been found to allow extraction of IgG from the waste precipitate without significant extraction of any of the other proteins present in the precipitate, which are considered to be impurities insofar as IgG purification is concerned. Thus, the solvent should be selected to be specific for removal of IgG from the precipitate, without simultaneously removing unwanted impurities from the precipitate.

The waste precipitate fraction can be subjected to a washing process immediately after it is produced. Alternatively, the waste fraction can be stored in frozen form for later processing. Before washing, the precipitate should, if necessary, be equilibrated to the temperature at which the washing process will be carried out. Such equilibration will generally be static, i.e. will not involve any agitation of the precipitate.

The type and amount of solvent used for the washing process should be selected such that recovery of IgG is maximised without unduly compromising the purity of the recovered IgG. To optimise IgG recovery whilst minimising extraction of impurities from the waste precipitate, the solvent used for the washing/extraction is preferably identical to the solvent used in the fractionation step which produced the waste precipitate in question.

When the waste fraction is (modified) Kistler & Nitschmann precipitate B or B+I, or Cohn fraction III or I+III preferred solvents are aqueous ethanol solutions. More preferably, such ethanol solutions are buffered. The ethanol concentration, temperature and pH should be controlled such that IgG extracted from the precipitate remains in solution.

Preferred concentrations of ethanol are in the range of about 10 to about 20 vol. %. More preferred is a concentration range of about 11 to about 19 vol. %, even more preferred is a concentration range of about 12 to about 19 vol. %, most preferably a concentration range of about 13 to about 17 vol. %. About 13 vol. % and about 17 vol. % are most preferred. "About 13 vol. %" is preferably 13±2 vol. %, whilst "about 17 vol. %" is preferably 17±2 vol. %.

The temperature at which the washing process occurs will also affect the amount and purity of the IgG recovered. Ideally, the temperature during the washing process is maintained at the same temperature that was used for the fractionation step which produced the waste precipitate in question. The optimum temperature range will therefore depend on the fraction and the fractionation process in question. Generally preferred are temperatures in the range of about −3° C. to about −8° C., including about −3° C. to about −7° C. For example, when the waste fraction is (modified) Kistler & Nitschmann precipitate B or B+I, the temperature during the washing extraction is preferably −5° C.±2.0° C. When the waste fraction is Cohn fraction III or I+III, the preferred temperature is usually slightly cooler, preferably −6° C.±2.0° C.

Generally preferred are temperatures in the range of about +3° C. to about −8° C., including about −3° C. to about −7° C. For example, when the waste fraction is modified Kistler & Nitschmann precipitate B or B+I, the temperature during the washing extraction is preferably −2° C.±5° C. When the waste fraction is Cohn fraction III or I+III, the preferred temperature is usually slightly cooler, preferably −3° C.±5.0° C.

The optimum pH range will also depend on the fraction. Generally preferred are pHs in the range of about 4.8 to about 5.3, more preferably about 5.1 to about 5.3. For example, when the waste fraction is (modified) Kistler & Nitschmann precipitate B or B+I, the pH range is preferably 5.1±0.05. When the waste fraction is Cohn fraction III or I+III, the pH may be slightly higher, preferably 5.2±0.05.

In a particularly preferred embodiment, when the waste fraction is (modified) Kistler & Nitschmann precipitate B or B+I, the solvent is 17±2 vol. % aqueous ethanol, the temperature is −5° C.±2.0° C. and the pH range is 5.1±0.05.

In a particularly preferred embodiment, when the waste fraction is (modified) Kistler & Nitschmann precipitate B or B+I, the solvent is 17±2 vol. % aqueous ethanol, the temperature is −2° C.±5° C. and the pH range is 5.1±0.05.

In another particularly preferred embodiment, when the waste fraction is Cohn fraction III or I+III, the solvent is 17±2 vol. % aqueous ethanol, the temperature is −6° C.±2.0° C. and the pH range is 5.2±0.05.

In another particularly preferred embodiment, when the waste fraction is Cohn fraction III or I+III, the solvent is 17±2 vol. % aqueous ethanol, the temperature is −3° C.±5° C. and the pH range is 5.2±0.05.

In another particularly preferred embodiment, when the waste fraction is (modified) Kistler & Nitschmann precipitate B or B+I prepared from hyperimmune plasma, or equivalent plasma, the solvent is 13±2 vol. % aqueous ethanol, the temperature is −5° C.±2.0° C. and the pH range is 5.1±0.05.

In another particularly preferred embodiment, when the waste fraction is (modified) Kistler & Nitschmann precipitate B or B+I prepared from hyperimmune plasma, or equivalent plasma, the solvent is 13±2 vol. % aqueous ethanol, the temperature is −2° C.±5° C. and the pH range is 5.1±0.05.

In another particularly preferred embodiment, when the waste fraction is Cohn fraction III or I+III prepared from hyperimmune plasma, or equivalent plasma, the solvent is 13±2 vol. % aqueous ethanol, the temperature is −6° C.±2.0° C. and the pH range is 5.2±0.05.

In another particularly preferred embodiment, when the waste fraction is Cohn fraction III or I+III prepared from hyperimmune plasma, or equivalent plasma, the solvent is 13±2 vol. % aqueous ethanol, the temperature is −3° C.±5° C. and the pH range is 5.2±0.05.

The solvent may be buffered using known buffers, including phosphate and acetate.

Figure 2:
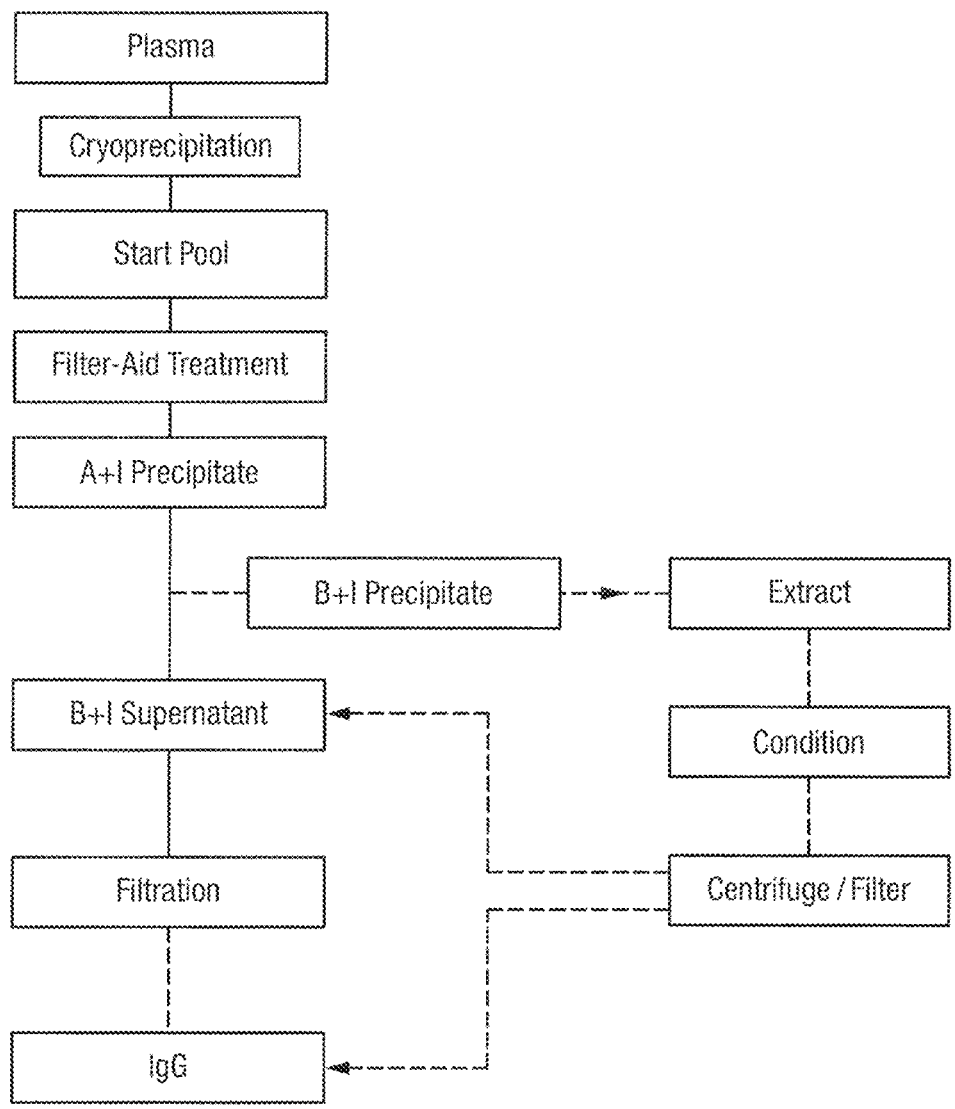
FIG. 2 is a schematic showing how a process of the invention can be integrated into a modified Kistler & Nitschmann cold ethanol fractionation process.
Figure 3:
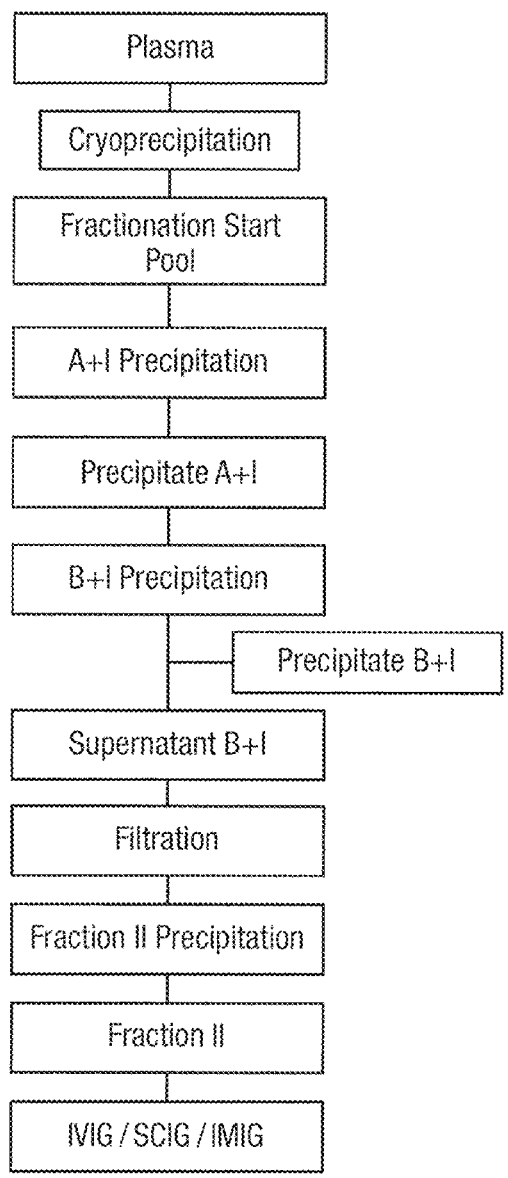
FIG. 3 is a schematic showing a modified Kistler & Nitschmann cold ethanol fractionation process for the production of IgG.

Generally, the washing step comprises suspension of the waste fraction in the solvent. The suspension is mixed, ideally until it is homogenised, and then left for a sufficient period of time for IgG to be extracted into the solvent. This corresponds to the "extract" and "condition" steps shown in FIGS. 2, 4 and 5. There is no specific upper time limit for this suspension/conditioning/extraction step. The time taken will in practice be limited by external factors such as process efficiency. For this reason, the extraction time is preferably between 1 and 24 hours, for example between about 2 and about 10 hours. A period of about 2 hours, e.g. 90-150 minutes, may also be suitable.

In a preferred aspect, the invention provides a method for the preparation of IgG comprising:
  a) recovering precipitate and supernatant from a modified Kistler and Nitschmann B+I fractionation process;
  b) homogenising the precipitate obtained in step a) and extracting IgG therefrom by mixing with 17 vol. % aqueous ethanol in acetate/phosphate buffer at 0° C. for 1 to 3 hours; and then
  c) separating the buffer containing extracted IgG from any remaining precipitate.

More preferably, the method above further comprises combining the buffer containing extracted IgG obtained in step c) with the modified Kistler and Nitschmann B+I supernatant obtained in step a). Alternatively, in the method described above, step c) is performed via filtration and the method further comprises incubating the extracted IgG in aqueous ethanol according to the conditions for modified Kistler and Nitschmann Fraction II precipitation; and recovering the resulting IgG-enriched Fraction II precipitate.

The IgG rich solution produced by the washing/extraction step preferably contains IgG of the same or similar purity to the main IgG-containing supernatant produced when the waste fraction was precipitated and/or separated away from the established IgG target protein manufacturing process stream.

Given the commercial and therapeutic value of IgG, any improvement in IgG yield from the starting plasma is potentially important, and even relatively low % recoveries of IgG from a waste fraction can be highly valuable.

The resulting IgG enriched solution may be recovered by any standard method known in the art, for example centrifugation or filtration to separate it from the remaining precipitate. If centrifugation is used, the supernatant will be IgG rich (i.e. will contain the extracted IgG), and the precipitate may be discarded, treated again according to the invention to extract further IgG and/or used for the extraction of other proteins. If filtration is used, the filtrate will be IgG rich, and the resultant filter cake may be discarded, further flushed to recover residual entrained IgG, treated again according to the invention to extract further IgG and/or used for the extraction of other proteins. Suitable filter media are known in the art. A silicate filter aid such as kieselghur, for example CELITE® or CELPURE®, may be added to facilitate filtration.

Any volume of solvent may potentially be used in the wash process, but should ideally be optimised for the available processing equipment. If very low volumes are used, the resulting suspension may be too viscous to process easily whilst very high volumes could lead to process inefficiencies. For reasons of process efficiency, it is therefore generally preferred to keep the volume of solvent relatively low. For example, the weight of waste fraction to solvent will generally be from about 1:2 to about 1:10. Preferably, the weight of solvent may be approximately four times the weight of the waste fraction, i.e. a weight ratio of about 1:4 of waste fraction to solvent.

The IgG rich solutions obtained using the processes of the invention can be further processed by methods known in the art to provide a pharmaceutically acceptable IgG product, according to the standards set by both the US and European Pharmacopoeia. Preferably, standard conditions are used to precipitate Fraction II from the solution, which is then further purified to provide a pharmaceutical product such as intravenous immunoglobulin (IVIG) or subcutaneous immunoglogulin (SCIG).

Further purification may take the form of anion and/or cation exchange chromatography, combined with suitable steps to assure the virus safety of the IVIG or SCIG (see Roberts et. al., Biologicals, Vol. 43(2), March 2015, p 123-129).

The IgG rich solution resulting from extraction from the waste fractions can be processed separately, combined with other solvent extraction of the same waste fractions and/or combined with the solvent extraction of the waste fractions from other process batches. However, it is generally more efficient to combine these solutions with the bulk IgG process intermediate of the main target protein downstream process. For example, the IgG from solvent extraction of the "waste fraction" may be combined with the IgG-rich supernatant from the fractionation step which produced the relevant waste precipitate. This may be the supernatant from the same fractionation batch, or a different batch.

Alternatively, the IgG extracted from the waste fraction may undergo one or more of the same downstream manufacturing steps as are used in the main IgG process, before being combined with the bulk IgG intermediate at a downstream process stage. For example, the IgG rich solution produced by washing/extraction from precipitate B+I may be combined with B+I supernatant which is then processed further to the final product. Alternatively, the IgG rich solution produced by washing/extraction from precipitate B+I may be processed through downstream process steps such as ethanol precipitation to Fraction II, before combining with the main IgG Fraction II intermediate processed from B+I supernatant and processing to the final product. Either option may be preferred, depending on the available scale of manufacturing equipment and associated logistics. The optimum solvent to be used for the extraction is may depend in part on any intended subsequent processing step(s).

Figure 4:
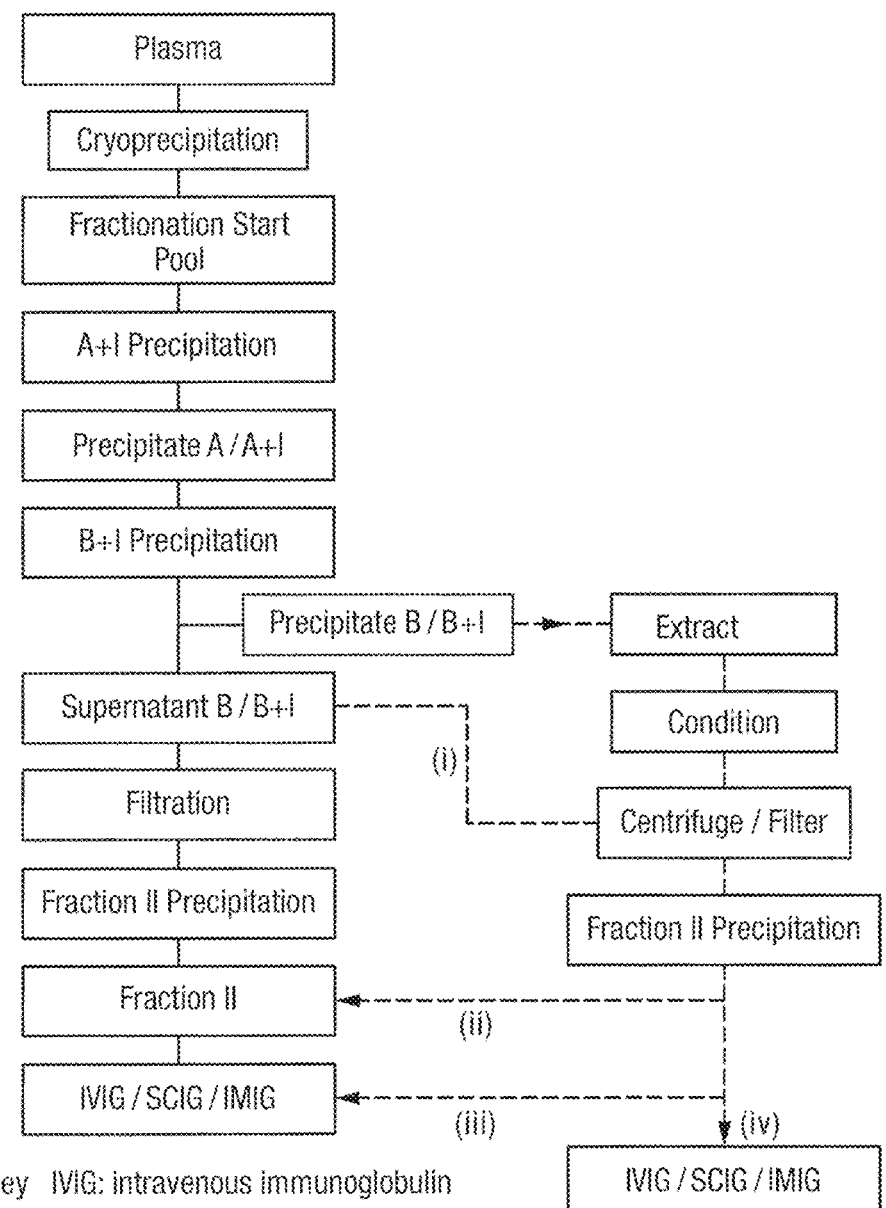
FIG. 4 is a schematic showing the modified Kistler & Nitschmann cold ethanol fractionation process of FIG. 3 incorporating an additional fraction B+I washing step of the present invention, with alternative stages for re-introduction of the additional recovered IgG into the process stream.
Figure 5:
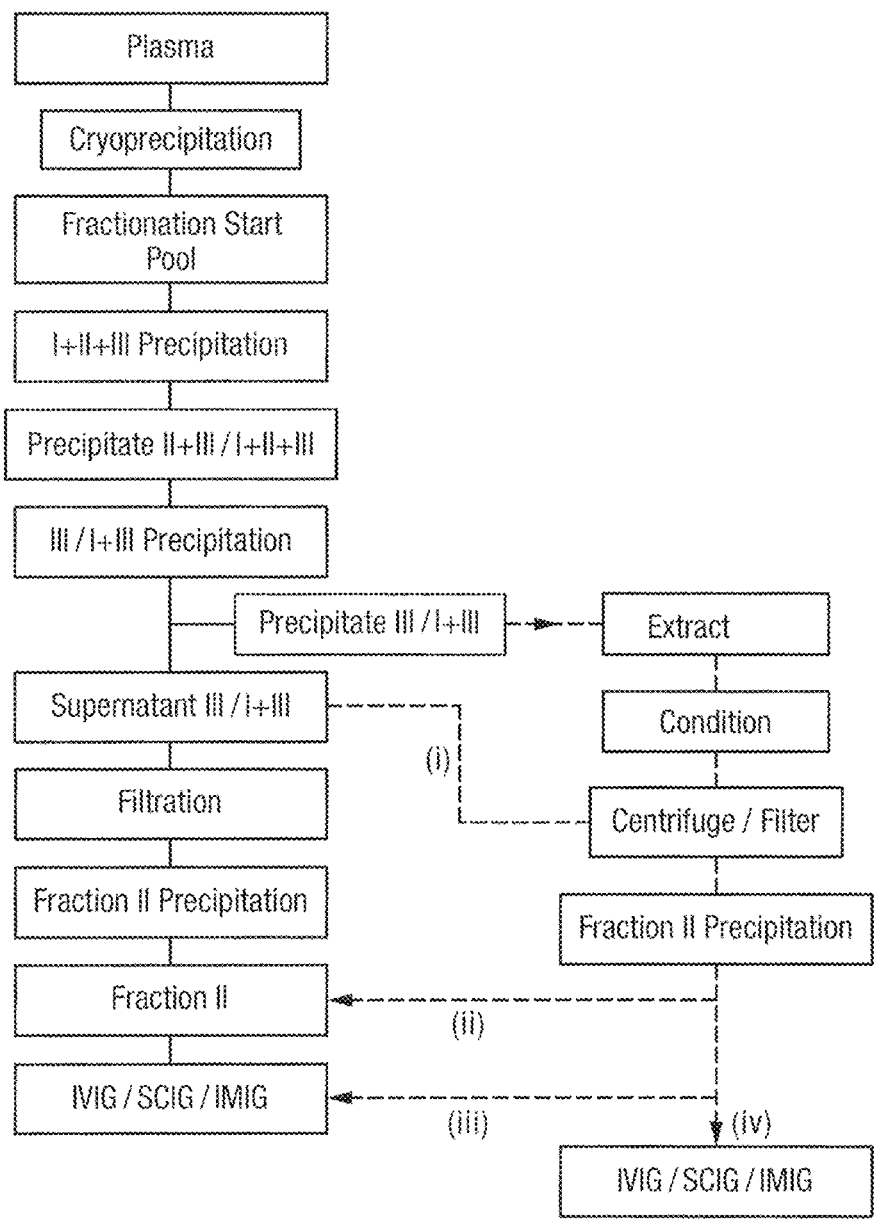
FIG. 5 is a schematic showing a Cohn/Oncley fractionation process with an additional fraction III/I+III washing step of the present invention, with alternative stages for re-introduction of the additional recovered IgG into the process stream.

Various alternative points at which the extracted IgG may be recombined with the main IgG process stream are shown in FIGS. 4 and 5.

Preferred features of the invention may be combined in any manner. Thus certain features which are, for clarity, described herein in the context of separate embodiments, may be combined in any manner. Conversely, various features that are, for brevity, described in the context of a single preferred feature, may also be provided separately or in any subcombination. Further, reference to values stated in ranges includes each and every value within that range.

Note that not all of the activities described above in the general description are required, that a portion of a particular activity may not be required, and that one or more further activities may be performed in addition to those described. Still further, the order in which activities are listed are not necessarily the order in which they are performed.

EXAMPLES

The following non-limiting Examples further illustrate the present invention.

In the following Examples/Tables, the precipitates and supernatants were analysed for protein content using a 'SpaPlus' auto-analyser (The Binding Site, Birmingham, UK), which is a turbidimetric analysis platform. Coagulation factors VII, IX, XI and XII were analysed using AssayPro ELISA kits (supplied by Universal Biologicals, Cambridge, UK). Factor XIa was measured using the Hyphen BioPhen chromogenic assay kit (supplied by Quadratech Diagnostics, Epsom, UK).

Table 1 below shows a typical composition of a B+I precipitate that is a waste fraction (equivalent to Cohn/Oncley Fraction III) produced by Kistler & Nitschmann cold-ethanol fractionation.

TABLE 1

| Protein | B + I precipitate | |
|---|---|---|
| | mg/litre plasma | % total |
| alpha 1 acid glycoprotein | 7 | 0.1 |
| alpha 1 antichymotrypsin | 31 | 0.5 |
| C1 inactivator | 12 | 0.2 |
| Ceruloplasmin | 195 | 3.2 |
| Antithrombin III | 77 | 1.3 |
| Prealbumin | 78 | 1.3 |
| B2 glycoprotein 1 | 16 | 0.3 |
| Gc Globulin | 51 | 0.8 |
| alpha 2 macroglobulin | 1240 | 20.6 |
| Haemopexin | 12 | 0.2 |
| alpha 1 antitrypsin | 51 | 0.8 |
| IgA | 1000 | 16.6 |
| IgG | 1100 | 18.3 |

TABLE 1-continued

| Protein | B + I precipitate | |
|---|---|---|
| | mg/litre plasma | % total |
| IgM | 710 | 11.8 |
| alpha 2 HS glycoprotein | 27 | 0.4 |
| Haptoglobin | 65 | 1.1 |
| Albumin | 204 | 3.4 |
| Fibrinogen | 457 | 7.6 |
| Apolipoprotein B | 506 | 8.4 |
| Inter alpha trypsin inhibitor | 168 | 2.8 |
| Transferrin | 9 | 0.1 |
| Total Protein | 6016 | 100 |

Starting material for the experiments described below was an IgG containing precipitate B+I, which had a composition similar to that shown in Table 1.

In the following examples, the 17 vol. % ethanol aqueous buffered solution is made as follows:

disodium hydrogen phosphate dihydrate 7.1 mM (1.27 g/L)

glacial acetic acid 12.8 mM (0.77 g/L)

17 vol. % ethanol in phosphate/acetate buffer: 141.6 g of 96% ethanol added to 858.4 g phosphate/acetate buffer (final pH is ~5.0-5.1).

Example 1

In a first experiment, 97 g of precipitate B+I was rapidly re-suspended by homogeniser at a pH of 4.8 to 5.2 in the presence of 1,000 g of a 17 vol. % ethanol aqueous buffered solution at a temperature range of about −3° C. to −7° C., to give a precipitate to buffer ratio of 1:10. The buffer consisted of 17 vol. % aqueous ethanol solution containing phosphate and acetate adjusted to the appropriate pH ("ethanol buffer").

In a second experiment, 99 g of the same precipitate B+I was re-suspended in the same manner in 1,000 g of 17 vol. % ethanol in water (i.e. unbuffered ethanol solution) at a temperature range of about −3° C. to −7° C. Both re-suspensions were then continuously mixed by moderate agitation and the precipitate was conditioned (matured) under the stated conditions over 24 hours. Samples of the buffered and non-buffered re-suspensions were centrifuged to recover the IgG enriched liquid. The pre-centrifuged suspension and the supernatant were analysed for the presence of IgG and several other proteins of interest (Table 2).

TABLE 2

Analysis of re-suspended precipitate B + I and supernatant fraction from buffered and unbuffered 17 vol. % aqueous ethanol solution

| | SAMPLES | 17 vol. % Ethanol in Phoshate/Acetate Buffer | | 17 vol. % Ethanol in Water | |
|---|---|---|---|---|---|
| | | Resuspension | Supernatant | Resuspension | Supernatant |
| Analysis | Turbidity (NTU) | | 23.5 | | 1,233 |
| | IgG (mg/mL) | 3.47 | 1.24 | 3.46 | 2.23 |
| | Albumin (mg/mL) | 0.76 | 0.33 | 0.81 | 0.28 |
| | IgA (mg/mL) | 1.67 | 0.03 | 1.94 | 0.43 |
| | IgM (mg/mL) | 0.85 | <0.11 | 0.94 | 0.25 |
| | Haptoglobin (mg/mL) | 0.06 | <0.025 | 0.06 | 0.03 |
| | FXIa (ng/mL) | 153 | <0.6 | 105 | 8.26 |
| | FXI (ng/mL) | 228 | <0.78 | 211 | 17.0 |
| | FXII (µg/mL) | 25.4 | 0.87 | 44.5 | 2.29 |
| | Protease (U/mL) | 547 | 7.22 | 425 | >50 |

TABLE 2-continued

Analysis of re-suspended precipitate B + I and supernatant fraction from buffered and unbuffered 17 vol. % aqueous ethanol solution

| SAMPLES | 17 vol. % Ethanol in Phosphate/Acetate Buffer | | 17 vol. % Ethanol in Water | |
|---|---|---|---|---|
| | Resuspension | Supernatant | Resuspension | Supernatant |
| Plasmin (IU/mL) | 0.45 | 0.11 | 0.40 | <0.1 |
| Plasminogen (U/mL) | NQ[a] | 0.09 | 0.43 | 0.79 |

[a] NQ = Not Quantifiable - sample OD between blank and lowest point of standard line
NTU = Nephelometric Turbidity Ratio Units, measured using a turbiditimeter calibrated in NTU From Table 2 it can be seen that re-suspension in both the phosphate/acetate buffered 17 vol. % aqueous ethanol solution ("ethanol buffer") and the unbuffered ethanol solution successfully extracted IgG. Unbuffered ethanol supernatant extract contained a higher concentration of IgG than the buffered supernatant, but buffered ethanol supernatant extract contained IgG with higher quality and much lower proportion of IgA and IgM. Protease activity, Factor XI/XIa and Factor XII were also lower in the buffered ethanol supernatant extract. High rates of thromboembolic side effects have been related to Factor XI and XIa in IVIG products and it is therefore highly desirable not to re-extract these into the supernatant fraction. Unlike the ethanol/water extract, the ethanol/buffer extract was similar in composition to the Supernatant B+I fraction (which goes on to Fraction II) and therefore admixing of the two fractions is possible to generate a single Fraction II of equivalent purity containing a higher yield of IgG.

The yield of IgG from the phosphate/acetate buffered aqueous ethanol supernatant was equivalent to 0.55 g of IgG per litre of plasma, which represents a yield increase of ~10% of the plasma IgG which can translate into 10-20% additional yield of the IgG final product.

Example 2

In a second set of experiments, the effect of reducing the re-suspension ratio was investigated to reduce the overall volume. In one experiment, 500 g of B+I precipitate was re-suspended in 1000 g of buffered aqueous ethanol solution (one part precipitate to two parts buffer). In another experiment 250 g of the same B+I precipitate was re-suspended in 1,000 g of ethanol buffer (one part precipitate to four parts buffer). Samples were taken at intervals during the maturation for analysis (Table 3).

TABLE 3

Effect of re-suspension ratio (precipitate:ethanol buffer) on quality of B + I suspension supernatant over 24 hours

| SAMPLES | | Maturation Time (Hours) | | | | | | | |
|---|---|---|---|---|---|---|---|---|---|
| | | 0.5 | | 2.0 | | 6.5 | | 24 | |
| | | Re-suspension ratio | | | | | | | |
| | Method | 1:2 | 1:4 | 1:2 | 1:4 | 1:2 | 1:4 | 1:2 | 1:4 |
| Analysis | Turbidity (NTU) | 3,432 | 27.2 | 3,314 | 28.1 | 4,000 | 47.9 | 3,765 | 30.7 |
| | IgG (mg/mL) | 4.98 | 2.69 | 4.69 | 2.78 | 3.97 | 2.85 | 4.30 | 1.83 |
| | Albumin (mg/mL) | 0.96 | 0.48 | 0.87 | 0.57 | 0.74 | 0.63 | 0.85 | 0.39 |
| | IgA (mg/mL) | 0.30 | 0.02 | 0.34 | 0.03 | 0.37 | 0.04 | 0.32 | <0.02 |
| | IgM (mg/mL) | 0.18 | <0.11 | 0.19 | <0.11 | 0.20 | <0.11 | 0.2.0 | <0.11 |
| | FXIa (ng/mL) | 5.20 | <0.6 | 5.20 | <0.6 | 6.65 | <0.6 | 5.85 | <0.6 |

The data in Table 3 indicate that ratios of 1:2 and 1:4 enable extraction of IgG from the precipitate and that the yield and quality of the extracted IgG was greater at the 1:4 ratio. For example, the turbidity of the 1:4 supernatants, which is a gross indicator of material quality, was two orders of magnitude lower than the equivalent 1:2 re-suspension supernatants. In addition, the concentrations of contaminants such as IgM, IgA and Factor XIa, were significantly decreased in 1:4 supernatant compared to 1:2 supernatant. Data from both experimental runs also suggest that the quality and yield of IgG can be maintained using maturation times of approximately two hours or more. The yield of IgG after 2 hour maturation was 0.47 g and 0.42 g of IgG per litre of plasma in the 1:4 and 1:2 supernatants respectively.

Example 3

Several re-suspensions were carried out at a 1:4 ratio to confirm the results of Example 2. A different batch of starting material was used in six re-suspensions. In each case, 250 g of B+I precipitate was re-suspended in 1,000 g of aqueous ethanol buffer as described above. The precipitate suspension was conditioned at −5° C. whilst mixing for a minimum of 2 hours. At the end of conditioning, the re-suspension was centrifuged. Both the re-suspension and the supernatant were analysed. The IgG concentration and IgG yield (plasma equivalent) of the supernatants were calculated (Table 4).

TABLE 4

IgG content and yield of confirmatory B + I re-suspensions

| | Confirmatory Runs 1:4 (B + I:Ethanol Buffer) | | | | | | |
|---|---|---|---|---|---|---|---|
| SAMPLE | 1 | 2 | 3 | 4 | 5 | 6 | MEAN |
| IgG (mg/mL) | 4.40 | 2.18 | 3.07 | 2.83 | 2.89 | 4.73 | 3.35 |
| Yield: IgG g/L PE | 0.75 | 0.35 | 0.52 | 0.48 | 0.49 | 0.8 | 0.57 |

The mean yield of IgG was 0.57 g IgG per litre of plasma. By addition to the main fractionation process stream, this yield can be translated into a significant yield increase, representing an additional 0.57 g IgG from each litre of plasma processed.

Example 4

334 g Of B+I precipitate was re-suspended in 1,335 g of 17 vol. % ethanol buffer and mixed for 2 hours at a temperature of −5° C. The liquid phase ("first extract") was then separated from the solid phase by centrifugation.

274 g of the solid phase precipitate was re-suspended in 1,096 g of 17 vol. % ethanol buffer and mixed for 2 hours at a temperature of −5° C. The liquid phase ("second extract") was then separated from the solid phase by centrifugation.

The pre-centrifuged suspension and the supernatant from each procedure were analysed for the presence of IgG and several other proteins of interest (Table 5). This confirmed that repeated sequential extractions of B+I precipitate yielded IgG in the solvent supernatant phase, with equivalent reduction in other proteins.

TABLE 5

| Sample | First Extract (supernatant) | Second Extract (supernatant) |
|---|---|---|
| IgG (mg/mL) | 4.22 | 2.17 |
| IgG (g per L plasma) | 0.71 | 0.40 |
| Albumin (mg/mL) | 0.95 | 0.60 |
| IgA (mg/mL) | 0.26 | 0.091 |
| IgM (mg/mL) | 0.18 | 0.12 |
| FXIa (ng/mL) | 2.40 | 1.31 |

Example 5

Extract of B+I precipitate was prepared by mixing one part of precipitate with four parts of 17 vol. % ethanol buffer for two hours at a temperature of −5° C. The extract was then separated from the residual precipitate by centrifugation.

The extract of B+I precipitate was then combined with B+I supernatant in a ratio of 1:10 by volume. The composition of the B+I supernatant was compared with the composition of the combined B+I supernatant and B+I precipitate extract (Table 6). This confirmed that the supernatant could be combined with the precipitate extract to increase the IgG concentration while retaining an acceptable IgG purity profile.

TABLE 6

| Sample | B + I Supernatant | B + I Supernatant + B + I precipitate extract |
|---|---|---|
| IgG (mg/mL) | 2.53 | 2.74 |
| Albumin (mg/mL) | 0.22 | 0.31 |
| IgA (mg/mL) | 0.02 | 0.04 |
| IgM (mg/mL) | <0.099 | <0.099 |
| FXIa (ng/mL) | <0.6 | <0.6 |
| FVII (ng/mL) | 4.65 | 6.75 |
| FIX (ng/mL) | 83.7 | 87.6 |
| FXII (ng/mL) | 260 | 603 |

Example 6

250 kg Of B+I precipitate from plasma fractionated according to the modified Kistler and Nitschmann method was conditioned at 0° C.±2° C. and resuspended by homogenisation at 0° C.±2° C. for one hour in the presence of 1000 kg 17 vol. % ethanol buffer. The mixture was then matured at 0° C.±2° C. for 2 hours, after which the pH was 5.14 and the conductivity was 0.6 mS/cm. The supernatant extract was separated from the precipitate by filtration or by centrifugation. This extraction method and recovery by either filtration or centrifugation successfully extracted IgG of high purity from the B+I precipitate (Table 7).

TABLE 7

| Sample | B + I Supernatant extract recovered by filtration | B + I Supernatant extract recovered by centrifugation |
|---|---|---|
| IgG (g/L) | 2.22 | 3.28 |
| IgG (g per L plasma) | 0.36 | 0.53 |
| Albumin (g/L) | 0.41 | 0.85 |
| IgA (g/L) | <0.02 | 0.1 |
| IgM (g/L) | <0.10 | <0.1 |
| FXIa (ng/mL) | NQ | 2.16 |
| Plasmin (U/mL) | <0.1 | <0.1 |
| Plasminogen (U/mL) | 0.15 | 0.3 |

Example 7

313 kg Of supernatant extract filtrate from Example 6 was adjusted to an ionic strength of 3.9 mS/cm, the ethanol concentration was raised to 25 vol. %, and the pH adjusted to pH 6.9 by titration with 1M sodium hydroxide and then incubated for 6 hours at −6.5° C. to yield 2.4 kg Fraction II precipitate which was collected by centrifugation. The Fraction II (Fr II) precipitate was dissolved in water (FrII: water=1:2). Analysis shows that the supernatant extract of B+I precipitate is compatible with further downstream purification to yield IgG with low levels of aggregate (Table 8).

TABLE 8

Composition of redissolved Fraction II precipitate from extracted B + I precipitate

| Sample | Redissolved FrII precipitate from extracted B + I precipitate |
|---|---|
| IG (g/L) | 88.1 |
| IgG (g per L plasma) | 0.32 |
| Albumin (g/L) | 6.91 |
| IgA (g/L) | 0.59 |
| IgM (g/L) | 0.23 |
| FXIa (ng/mL) | 1.51 |
| Plasmin (U/mL) | <0.1 |
| Plasminogen (U/mL) | 0.16 |
| % aggregate (by HPLC) | 1.31 |

Example 8

100 g Of B+I precipitate which had been stored frozen at less than −30° C. was brought to 0° C. without any agitation either in a vessel controlled to 0° C. (option (a)) or in a vessel containing 17 vol. % ethanol buffer which was controlled to 0° C. (option (b)). The temperature was measured by probes which had been placed in the precipitate before freezing. When the precipitate temperature reached 0° C.±1° C., 17 vol. % ethanol buffer was added to the precipitate from option (a) and both precipitates were homogenised prior to extraction of IgG into the solvent buffer with agitation for not less than 2 hours (maturation/conditioning). The supernatant was then separated from the remaining precipitate and analysed. There was equivalent IgG extraction from precipitate when conditioned to 0° C. with or without buffer (Table 9).

TABLE 9

| | Supernatant extract from B + I precipitate conditioned to 0° C. | |
|---|---|---|
| Sample | Without buffer | With buffer |
| IgG (g/L) | 5.21 | 5.40 |
| IgG (g per L plasma) | 0.87 | 0.94 |
| Albumin (g/L) | 1.51 | 1.73 |
| IgA (g/L) | 0.33 | 0.50 |
| IgM (g/L) | 0.32 | 0.44 |
| FXIa (ng/mL) | 8.14 | 11.6 |
| Plasmin (U/mL) | 0.22 | 0.19 |
| Plasminogen (U/mL) | 0.57 | 1.23 |

The invention claimed is:

1. A method for extracting IgG from a waste precipitate fraction, the method comprising homogenizing the waste precipitate fraction with a suitable solvent for a period sufficient to extract IgG from the precipitate into the solvent, wherein the waste precipitate fraction is produced during plasma fractionation and separated from a main IgG manufacturing process stream, and wherein the suitable solvent is the same as a solvent used in a fractionation step which produced the waste precipitate wherein the extracted IgG comprises not less than 85% monomer and dimer and not more than 10 wt. % polymer and/or aggregate, and wherein the method for extracting IgG from the waste precipitate fraction does not involve any chromatographic steps.

2. A method according to claim 1, wherein the waste precipitate fraction is produced during a fractionation step to produce a liquid fraction (supernatant) containing IgG.

3. A method according to claim 2, wherein the liquid fraction is selected from the group consisting of Cohn supernatant III, Cohn supernatant I+III, Kistler & Nitschmann supernatant B, Kistler & Nitschmann supernatant B+I, modified Kistler & Nitschmann supernatant B, and modified Kistler & Nitschmann supernatant B+I.

4. A method according to claim 1, wherein the waste precipitate fraction is selected from the group consisting of Cohn fraction III, Cohn fraction I+III, Kistler & Nitschmann precipitate B, Kistler & Nitschmann precipitate B+I, modified Kistler & Nitschmann precipitate B, and modified Kistler & Nitschmann precipitate B+I.

5. A method according to claim 1, wherein the solvent is buffered aqueous ethanol.

6. A method according to claim 5, wherein the solvent is an aqueous buffer containing about 13 vol. % to about 17 vol. % ethanol.

7. A method according to claim 5, wherein the solvent is buffered using phosphate and/or acetate buffer.

8. A method according to claim 1, wherein the ratio of waste precipitate fraction to solvent is from about 1:2 to about 1:10.

9. A method according to claim 1, wherein the solvent containing extracted IgG is separated from any remaining waste precipitate solids.

10. A method according claim 9, wherein the solvent containing extracted IgG is separated from remaining waste precipitate solids by filtration or centrifugation.

11. A method according to claim 1, wherein the extracted IgG is combined with IgG obtained from the main IgG manufacturing process stream.

12. A method according to claim 1, wherein the method for extracting IgG from the waste precipitate fraction does not involve any chromatographic steps.

13. A method according to claim 1, wherein the extracted IgG obtained from the waste precipitate is further processed to produce a pharmaceutical IgG product.

14. A method according to claim 13, wherein the further processing to produce a pharmaceutical IgG product comprises precipitation of the extracted IgG from the solvent.

15. A method according to claim 14, wherein the precipitation is achieved by adjusting one or more of ethanol concentration, temperature and pH.

16. A method according to claim 14, wherein the precipitation yields an IgG enriched Fraction II precipitate.

17. A method according to claim 14, wherein the resulting precipitate is combined with an IgG rich fraction from the main IgG manufacturing process stream.

18. A method for the preparation of IgG comprising:
a) recovering precipitate and supernatant from a modified Kistler and Nitschmann B+I fractionation process;
b) homogenising the precipitate obtained in step a) and extracting IgG therefrom by mixing with 17 vol. % aqueous ethanol in acetate and/or phosphate buffer at 0°

C. for 1 to 3 hours, and wherein extracting IgG does not involve any chromatographic steps; and then c) separating the buffer containing extracted IgG from any remaining precipitate, wherein the extracted IgG comprises not less than 85% monomer and dimer and not more than 10 wt. % polymer and/or aggregate.

19. The method according to claim 18, further comprising:

d) combining the buffer containing extracted IgG obtained in step c) with the modified Kistler and Nitschmann B+I supernatant obtained in step a).

20. The method according to claim 18, wherein step c) is performed via filtration and wherein the method further comprises:

e) incubating the extracted IgG in aqueous ethanol according to the conditions for modified Kistler and Nitschmann Fraction II precipitation; and f) recovering the resulting IgG-enriched Fraction II precipitate.

21. A method according to claim 1, wherein the extracted IgG product comprises a purity of not less than 90% gammaglobulin.

\* \* \* \* \*